(12) United States Patent
Zhong et al.

(10) Patent No.: US 7,678,921 B2
(45) Date of Patent: Mar. 16, 2010

(54) METHOD FOR THE ENANTIOMOERIC SEPARATION OF OPTICAL ACTIVE AMLODIPINE

(75) Inventors: Nanping Zhong, Shijiazhuang (CN); Xianfeng Zhao, Shijiazhuang (CN); Hui Ma, Shijiazhuang (CN); Yujie Chen, Shijiazhuang (CN)

(73) Assignee: Shijiazhuang Pharmaceutical Group Ouyl Pharma. Co., Ltd. (CN)

( * ) Notice: Subject to any disclaimer, the term of this patent is extended or adjusted under 35 U.S.C. 154(b) by 897 days.

(21) Appl. No.: 10/596,209

(22) PCT Filed: Dec. 3, 2004

(86) PCT No.: PCT/CN2004/001412

§ 371 (c)(1), (2), (4) Date: Jun. 2, 2006

(87) PCT Pub. No.: WO2005/054196

PCT Pub. Date: Jun. 16, 2005

(65) Prior Publication Data

US 2007/0093661 A1    Apr. 26, 2007

(30) Foreign Application Priority Data

Dec. 5, 2003    (CN) .................... 2003 1 0119335

(51) Int. Cl.
*C07D 211/86* (2006.01)
(52) U.S. Cl. .................................... 546/321
(58) Field of Classification Search ............ None
See application file for complete search history.

(56) References Cited

U.S. PATENT DOCUMENTS 6,057,344 A    5/2000    Young

FOREIGN PATENT DOCUMENTS

| CN | 1067055 C | 6/2001 |
|---|---|---|
| CN | 1100038 C | 1/2003 |
| EP | 0331315 A2 | 9/1989 |
| WO | WO 9525722 A1 * | 9/1995 |
| WO | WO 03035623 A1 | 5/2003 |

OTHER PUBLICATIONS

US Department of Heath and Human Services, FDA, Guidance for the Industry, Q3C-Tables and List, pp. 1-10, Nov. 2003.*
International Search Report for International Application No. PCT/CN2004/001412 dated Mar. 17, 2005 (3 pages).
"Enantiomoeric Separation of Amlodipine by High Performance Capillary Electrophoresis," Journal of Analytical Science, vol. 19, No. 1, Feb. 2003, pp. 33-35.

* cited by examiner

*Primary Examiner*—Zinna N Davis
(74) *Attorney, Agent, or Firm*—Fitch, Even, Tabin & Flannery

(57) ABSTRACT

The present invention relates to the preparation of the (S)-(−)-amlodipine and (R)-(+)-amlodipine by means of enantiomeric separation of racemic amlodipine mixture, in which, L- or D-tartaric acid is used as resolution agent, and organic solvent containing 2-butanone is used as solvent. The 2-butanone used in the present invention has the advantage of low boiling point, low toxicity, litter pollution, and the method is suitable for large-scaled production.

12 Claims, No Drawings

METHOD FOR THE ENANTIOMOERIC SEPARATION OF OPTICAL ACTIVE AMLODIPINE

This application is a 371 of PCT/CN04/01412 filed Dec. 3, 2004.

TECHNICAL FIELD

The present invention relates to a method for the chemical resolution of racemic amlodipine.

BACKGROUND ART

Amlodipine is a calcium ion antagonist, which is used for clinically treating hypertension and stable angina. Currently, amlodipine clinically used is substantially the raceme thereof. It is reported that the main pharmacological active ingredient in the raceme is (S)-(−)-amlodipine and the antagonistic activity thereof against calcium ion is about 1000 times to that of (R)-(+)-amlodipine and double to that of the raceme per se by Arrowsmiith, J. E. et al., J. Med. Chem. (1986) 29; 1696-1702. WO93/10779 (Young, J. W.) discloses that the administration of (S)-(−)-amlodipine can reduce the side effects such as acroedema, headache, dizziness etc. as compared with using racemic amlodipine. Accordingly, the therapies of hypertension and stable angina by administrating (S)-(−)-amlodipine have a good market prospect. The other enantiomer, (R)-(+)-amlodipine, has the activity of treating atherosclerosis.

The chemical structure formula of amlodipine is showed by

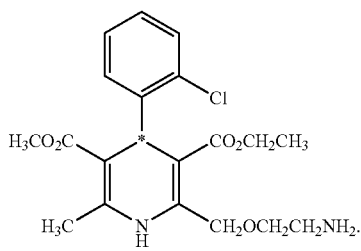

The method for preparing the enantiomers of amlodipine essentially comprises the resolution of racemic amlodipine. WO95/25722 (Pfizer Pharmaceuticals Limited) provides a method for obtaining the enantiomers of amlodipine by direct resolution of amlodipine using D- or L-tartaric acid as resolving agent and dimethyl sulphoxide (DMSO) as solvent, which has a disadvantage in that a high boiling point of DMSO solvent, i.e. 189° C., tends to cause the recovery of solvent is difficult during the preparation. WO 03/035623 (Sepracor Co.) describes a method for directly resolving racemic amlodipine by using D- or L-tartaric acid as resolving agent and N,N-dimethyl acetamide (DMAC) as solvent. Similarly, it is difficult to recover DMAC due to the high boiling point of about 164-166° C. And since DMAC belongs to the Second Solvent which has high toxicity (Guidance for Industry IMPURITIES: RESIDUAL SOLVENTS, FDA, May 15, 2001), it tends to result in the serious environmental contamination during the preparation.

SUMMARY OF THE INVENTION

The present invention intends to find a method for producing the enantiomers of amlodipine in industrial scale.

The present invention provides a method for preparing (S)-(−)-amlodipine and (R)-(+)-amlodipine from racemic amlodipine.

In one embodiment, racemic amlodipine and L-(+)-tartaric acid are dissolved in an organic solvent containing 2-butanone to yield (S)-(−)-amlodipine-L-(+)-tartrate precipitate by reaction. After the precipitate is separated, a solid is obtained by recrystallization with a lower alcohol solvent. Subsequently a lower alkyl halide is added into the solid and the resulting solution is neutralized by an aqueous alkali to give (S)-(−)-amlodipine.

The organic solvent is 2-butanone or mixture of 2-butanone with a cosolvent.

The cosolvent may be selected from the group consisting of methanol, ethanol, n-butanol, acetone, 2-pentanone, ethyl ether, methyl ethyl ether, ethyl acetate, ethyl formate, dichloromethane and chloroform.

The molar ratio of racemic amlodipine to L-(+)-tartaric acid is 1:0.25~0.8, preferably is 1:0.5.

The lower alcohol solvent is selected from the group consisting of ethanol, methanol and isopropanol.

In another embodiment, racemic amlodipine and D-(−)-tartaric acid are dissolved in an organic solvent containing 2-butanone to yield (R)-(+)-amlodipine-D-(−)-tartrate precipitate by reaction. After the precipitate is separated, a solid is obtained by recrystallization with a lower alcohol solvent. Subsequently a lower alkyl halide is added into the solid and the resulting solution is neutralized by an aqueous alkali to give (R)-(+)-amlodipine.

The organic solvent is 2-butanone or mixture of 2-butanone with a cosolvent.

The cosolvent may be selected from the group consisting of methanol, ethanol, n-butanol, acetone, 2-pentanone, ethyl ether, methyl ethyl ether, ethyl acetate, ethyl formate, dichloromethane and chloroform.

The molar ratio of racemic amlodipine to D-(−)-tartaric acid is 1:0.25~0.8, preferably is 1:0.5.

The lower alcohol solvent is selected from the group consisting of ethanol, methanol and isopropanol.

A detecting method for the enantiomers of amlodipine comprises determining the optical purity by chiral column HPLC in which a chiral column of Ultron ES-OVM is used (egg mucoprotein: 15 cm; flow rate: 1 ml/min; detecting wavelength: 360 nm; mobile phase: 0.02 mol/L sodium hydrogen phosphate (pH7): acetonitrile=80:20). Samples are dissolved in a solution of acetonitrile and water (50:50, 0.2 mg/ml).

2-Butanone having a boiling point of 80° C. as used in the present invention can be readily recovered after applying in large amount, and it belongs to the Third solvent (Guidance for Industry IMPURITIES: RESIDUAL SOLVENTS, FDA, May 15, 2001), which is suitable for large-scaled production due to low toxicity and little environmental contamination.

DETAILED MODES OF EMBODIMENTS

In a preferred embodiment, racemic amlodipine and L-(+)-tartaric acid are dissolved in an organic solvent containing sufficient amount of 2-butanone, wherein a preferred molar ratio of racemic amlodipine to L-(+)-tartaric acid is 1:0.5. And the organic solvent contains any amount of 2-butanone as long as racemic amlodipine and L-(+)-tartaric acid can be sufficiently dissolved, wherein a preferred amount of 2-butanone is more than 50% by volume of the organic solvent. (S)-(−)-amlodipine-L-(+)-tartrate precipitate produced by the reaction is filtered out and the resulting solid is recrystallized by using ethanol preferably, and then neutralized by aqueous NaOH to give (S)-(−)-amlodipine.

In another preferred embodiment, racemic amlodipine and D-(−)-tartaric acid are dissolved in an organic solvent containing sufficient amount of 2-butanone, wherein a preferred molar ratio of racemic amlodipine to D-(−)-tartaric acid is 1:0.5. And the organic solvent contains any amount of 2-butanone as long as racemic amlodipine and D-(−)-tartaric acid can be sufficiently dissolved, wherein a preferred amount of 2-butanone is more than 50% by volume of the organic solvent. (R)-(+)-amlodipine-D-(−)-tartrate precipitate produced by the reaction is filtered out and the resulting solid is recrystallized by using ethanol preferably, and then neutralized by aqueous NaOH to give (R)-(+)-amlodipine.

EXAMPLE 1

Preparation of (S)-(−)-amlodipine 5 g (0.012 mol) of amlodipine was dissolved in 40 ml of 2-butanone, and 1.0 g (0.06 mol) L-(+)-tartaric acid dissolved with 60 ml of 2-butanone was added thereto and then reacted for 1 hour under stirring at room temperature. The precipitate was separated out and filtered, and then washed with small quantity of 2-butanone to give 2.1 g of solid. The mother solution was distilled in order to recover 2-butanone. Subsequently the resulting solid is recrystallized by using ethanol to give 1.7 g of (S)-(−)-amlodipine-L-(+)-tartrate.

18 ml of dichloromethane and 10 ml of 2N aqueous NaOH were added into 1.7 g of (S)-(−)-amlodipine-L-(+)-tartrate, then reacted for 30 minutes under stirring. The solution was kept standing until organic phase is separated out. The organic phase was dried by adding anhydrous sodium carbonate and then filtered. The filter cake was washed with small amount of dichloromethane. The filter solution together with the washed dichloromethane were concentrated under reduced pressure, then crystallized under stirring and filtered following by adding n-hexane. The crystal thus obtained was dried under vacuum overnight to give 1.2 g of (S)-(−)-amlodipine. Enantiomeric excess (ee) determined by chiral column HPLC is 99.0% and yield is 48%.

EXAMPLE 2

Preparation of (R)-(+)-amlodipine 5 g (0.012 mol) of amlodipine was dissolved in 40 ml of 2-butanone, and 1.0 g (0.06 mol) D-(−)-tartaric acid dissolved with 50 ml of 2-butanone was added thereto and then reacted for 1 hour under stirring at room temperature. The precipitate was separated out and filtered, and then washed with small quantity of 2-butanone to give 2.3 g of solid. The mother solution was distilled in order to recover 2-butanone. Subsequently the resulting solid is recrystallized by using ethanol to give 1.8 g of (R)-(+)-amlodipine-D-(−)-tartrate.

20 ml of dichloromethane and 10 ml of 2N aqueous NaOH were added into 1.8 g of (R)-(+)-amlodipine-D-(−)-tartrate, then reacted for 30 minutes under stirring. The solution was kept standing until organic phase is separated out. The organic phase was dried by adding anhydrous sodium carbonate and then filtered. The filter cake was washed with small amount of dichloromethane. The filter solution together with the washed dichloromethane were concentrated under reduced pressure, then crystallized under stirring and filtered following by adding n-hexane. The crystal thus obtained was dried under vacuum overnight to give 1.3 g of (R)-(+)-amlodipine Enantiomeric excess (ee) determined by chiral column HPLC is 98.8% and yield is 52%.

EXAMPLE 3

Preparation of (S)-(−)-amlodipine

The preparation of (S)-(−)-amlodipine is in a same way as Example 1, except that the amount of L-(+)-tartaric acid was varied to 0.5 g, so as to give 0.9 g of (S)-(−)-amlodipine. Enantiomeric excess (ee) determined by chiral column HPLC is 98.7%.

EXAMPLE 4

Preparation of (S)-(−)-amlodipine

The preparation of (S)-(−)-amlodipine is in a same way as Example 1, except that the amount of L-(+)-tartaric acid was varied to 1.6 g, so as to give 1.0 g of (S)-(−)-amlodipine. Enantiomeric excess (ee) determined by chiral column HPLC is 95.2%.

EXAMPLE 5

Preparation of (S)-(−)-amlodipine

The preparation of (S)-(−)-amlodipine is in a same way as Example 1, except that the solvent was replaced with a mixing solvent of the cosolvents listed in following table with 2-butanone.

TABLE 1

| cosolvent | volume of cosolvent $(V_{cosolvent}/V_{total\ solvent})\%$ | ee % of (S)-(−)-amlodipine |
|---|---|---|
| water | 0.1 | 98.5 |
| ethanol | 1 | 95.2 |
| acetone | 1 | 96 |
| ethyl acetate | 5 | 94.3 |
| dichloromethane | 3 | 95.6 |

It will be appreciated by person skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method for preparing (S)-(−)-amlodipine comprising: dissolving racemic amlodipine and L-(+)-tartaric acid in an organic solvent containing 2-butanone to yield (S)-(−)-amlodipine-L-(+)-tartrate precipitate by reaction; separating the precipitate; recrystallizating the precipitate by using a lower alcohol solvent to obtain a solid; adding a lower alkyl halide into the solid; and neutralizing with an aqueous alkali to give (S)-(−)-amlodipine.

2. The method for preparing (S)-(−)-amlodipine according to claim 1, wherein said organic solvent is 2-butanone or mixture of 2-butanone with a cosolvent.

3. The method for preparing (S)-(−)-amlodipine according to claim 2, wherein said cosolvent is selected from the group consisting of methanol, ethanol, n-butanol, acetone, 2-pentanone, ethyl ether, methyl ethyl ether, ethyl acetate, ethyl formate, dichloromethane and chloroform.

4. The method for preparing (S)-(−)-amlodipine according to claim 1, wherein the molar ratio of racemic amlodipine to L-(+)-tartaric acid is 1:0.25~0.8.

5. The method for preparing (S)-(−)-amlodipine according to claim 4, wherein the molar ratio of racemic amlodipine to L-(+)-tartaric acid is 1:0.5.

6. The method for preparing (S)-(−)-amlodipine according to claim 1, wherein said lower alcohol solvent is selected from the group consisting of ethanol, methanol and isopropanol.

7. A method for preparing (R)-(+)-amlodipine comprising: dissolving racemic amlodipine and D-(−)-tartaric acid in an organic solvent containing 2-butanone to yield (R)-(+)-amlodipine-D-(−)-tartrate precipitate by reaction; separating the precipitate; recrystallizating the precipitate by using a lower alcohol solvent to obtain a solid; adding a lower alkyl halide into the solid; and neutralizing with an aqueous alkali to give (R)-(+)-amlodipine.

8. The method for preparing (R)-(+)-amlodipine according to claim 7, wherein said organic solvent is 2-butanone or mixture of 2-butanone with a cosolvent.

9. The method for preparing (R)-(+)-amlodipine according to claim 8, wherein said cosolvent is selected from the group consisting of methanol, ethanol, n-butanol, acetone, 2-pentanone, ethyl ether, methyl ethyl ether, ethyl acetate, ethyl formate, dichloromethane and chloroform.

10. The method for preparing (R)-(+)-amlodipine according to claim 7, wherein the molar ratio of racemic amlodipine to D-(−)-tartaric acid is 1:0.25~0.8.

11. The method for preparing (R)-(+)-amlodipine according to claim 10, wherein the molar ratio of racemic amlodipine to D-(−)-tartaric acid is 1:0.5.

12. The method for preparing (R)-(+)-amlodipine according to claim 7, wherein said lower alcohol solvent is selected from the group consisting of ethanol, methanol and isopropanol.

* * * * *

UNITED STATES PATENT AND TRADEMARK OFFICE
CERTIFICATE OF CORRECTION

PATENT NO. : 7,678,921 B2  Page 1 of 1
APPLICATION NO. : 10/596209
DATED : March 16, 2010
INVENTOR(S) : Nanping Zhong et al.

It is certified that error appears in the above-identified patent and that said Letters Patent is hereby corrected as shown below:

Title Page, item [73]:

change "Shijiazhuang Pharmaceutical Group Ouyl Pharma. Co., Ltd." to -- Shijiazhuang Pharmaceutical Group Ouyi Pharma. Co., Ltd. --.

Signed and Sealed this

Twenty-sixth Day of October, 2010

David J. Kappos
*Director of the United States Patent and Trademark Office*